(12) United States Patent
Wesemann et al.

(10) Patent No.: US 9,082,990 B2
(45) Date of Patent: Jul. 14, 2015

(54) COMPLEX COMPOUNDS HAVING A LIGAND CONTAINING AN N DONOR AND A P DONOR AND THE USE THEREOF IN THE OPTO-ELECTRONIC FIELD

(75) Inventors: Lars Wesemann, Tuebingen (DE); Fritz-Robert Kuechle, Boos, DE (US); Hermann August Mayer, Tuebingen (DE); Sophie Wernitz, Köln (DE); Hartmut Yersin, Sinzing (DE); Markus Leitl, Regensburg (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 14/234,781

(22) PCT Filed: Jul. 19, 2012

(86) PCT No.: PCT/EP2012/064235
§ 371 (c)(1),
(2), (4) Date: Mar. 13, 2014

(87) PCT Pub. No.: WO2013/014066
PCT Pub. Date: Jan. 31, 2013

(65) Prior Publication Data
US 2014/0213806 A1     Jul. 31, 2014

(30) Foreign Application Priority Data
Jul. 26, 2011  (DE) .................. 10-2011-079-856

(51) Int. Cl.
*H01L 51/00*  (2006.01)
*C09K 11/06*  (2006.01)
(Continued)

(52) U.S. Cl.
CPC .............. *H01L 51/009* (2013.01); *C07F 1/08* (2013.01); *C09K 11/06* (2013.01);
(Continued)

(58) Field of Classification Search
CPC ........ C07F 1/08; C07F 11/00; C07F 15/0006; C07F 15/0013; H01L 51/009; H01L 51/0091; H01L 51/5012; H05B 33/14; C09K 11/06; C09K 11/1096

USPC .......................... 556/43, 23; 438/99
See application file for complete search history.

(56) References Cited

U.S. PATENT DOCUMENTS 6,963,005 B2   11/2005  Lecloux et al.
7,683,183 B2    3/2010  Peters et al.
(Continued)

FOREIGN PATENT DOCUMENTS

CN    101747375 A    6/2010
DE   102008033563 A1  1/2010
(Continued)

OTHER PUBLICATIONS

U.S. Appl. No. 14/234,809, filed Jan. 24, 2014, Wesemann et al.
(Continued)

*Primary Examiner* — Porfirio Nazario Gonzalez
(74) *Attorney, Agent, or Firm* — Drinker Biddle & Reath LLP

(57) ABSTRACT

The invention describes electronic devices comprising a metal complex compound having at least one ligand containing an N donor and a P donor having the formula (I), in which the carbons C1 and C2 are part of an aromatic or non-aromatic ring system F1, P and N are phosphorus and nitrogen, where the nitrogen is in sp2-hybridized form, the radicals R3 and R4 are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and R1 and R2 are, independently of one another, an atom or radical from the group comprising hydrogen, halogen, R, RO—, RS—, RCO—, RCOO—, RNH—, R2N—, RCONR— and —Si(R)X(OR)3-X, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3. The invention furthermore describes a process for the production of an electronic device of this type and processes for the generation of light or blue emission using a metal complex compound of this type.

14 Claims, 3 Drawing Sheets

(51) Int. Cl.
*H05B 33/14* (2006.01)
*C07F 1/08* (2006.01)
*H01L 51/50* (2006.01)

(52) U.S. Cl.
CPC ....... *H01L 51/0004* (2013.01); *H01L 51/0091* (2013.01); *H05B 33/14* (2013.01); *C09K 2211/1096* (2013.01); *H01L 51/5012* (2013.01); *Y02E 10/549* (2013.01)

(56) References Cited

U.S. PATENT DOCUMENTS

| | | |
|---|---|---|
| 2002/0048689 A1 | 4/2002 | Igarashi et al. |
| 2005/0244672 A1 | 11/2005 | Che et al. |
| 2007/0111026 A1 | 5/2007 | Deaton et al. |
| 2007/0265473 A1 | 11/2007 | Becker et al. |
| 2008/0036370 A1 | 2/2008 | Noh et al. |
| 2010/0026174 A1 | 2/2010 | Igarashi et al. |
| 2010/0227974 A1 | 9/2010 | Schulte et al. |
| 2011/0108769 A1 | 5/2011 | Yersin et al. |
| 2011/0144366 A1 | 6/2011 | Stoessel et al. |
| 2011/0155954 A1 | 6/2011 | Yersin et al. |

FOREIGN PATENT DOCUMENTS

| | | |
|---|---|---|
| EP | 1424350 | 6/2004 |
| JP | 2003212886 A | 7/2003 |
| WO | WO-2004/041901 | 5/2004 |
| WO | WO-2005/118606 A1 | 12/2005 |
| WO | WO-2008/019744 A1 | 2/2008 |
| WO | WO-2010006681 A1 | 1/2010 |
| WO | WO-2011063083 A1 | 5/2011 |

OTHER PUBLICATIONS

U.S. Appl. No. 14/234,710, filed Jan. 24, 2014, Wesemann et al.
U.S. Appl. No. 14/234,857, filed Jan. 24, 2014, Wesemann et al.
Cheng, Yi-Ming, et al., "Rational Design of Chelating Phosphine Functionalized $Os^{(II)}$ Emitters and Fabrication of Orange Polymer Light-Emitting Diodes Using Solution Process", Adv. Funct. Mater., vol. 18, (2008), pp. 83-194.
Deaton, Joseph C., et al., "E-Type Delayed Fluorescence of a Phosphine-Supported $Cu_2(\mu-NAr_2)_2$ Diamond Core: Harvesting Singlet and Triplet Excitons in OLEDsII", J. Am. Chem. Soc., vol. 132, (2010), pp. 9499-9508.
Kui, Steven C.F., et al., "Platinum(II) Complexes with □-Conjugated, Naphthyl-Substituted, Cyclometalated Ligands (RC□N □N): Structures and Photo- and Electroluminescence", Chem. Eur. J., vol. 13, (2007), pp. 417-435.
Miller, Alexander J.M., et al., "Long-Lived and Efficient Emission from Mononuclear Amidophosphine Complexes of Copper", Inorganic Chemistry, vol. 46, No. 18, (2007), pp. 7244-7246.
Moudam, Omar, et al., "Electrophosphorescent Homo- and Heteroleptic Copper(I) Complexes Prepared from Various Bis-Phosphine Ligands", Chem. Commun., (2007), pp. 3077-3079.
International Search Report for PCT/EP2012/064235 mailed Oct. 2, 2012.

COMPLEX COMPOUNDS HAVING A LIGAND CONTAINING AN N DONOR AND A P DONOR AND THE USE THEREOF IN THE OPTO-ELECTRONIC FIELD

CROSS-REFERENCE TO RELATED APPLICATIONS

This application is a national stage application (under 35 U.S.C. §371) of PCT/EP2012/064235, filed Jul. 19, 2012, which claims benefit of German application 10 2011 079 856.0, filed Jul. 26, 2011.

The present invention relates to electronic devices, such as organic electroluminescent devices (OLEDs), light-emitting electrochemical cells (LEECs), organic solar cells (OSCs), organic field-effect transistors and organic lasers, which comprise organotransition-metal complex compounds as light emitters and/or light absorbers. Some particularly suitable complex compounds and the use thereof in the opto-electronic field are described.

Organotransition-metal complex compounds are important building blocks for opto-electronic devices, such as organic solar cells or organic electroluminescent devices. This applies, in particular, to compounds which are able to function as triplet emitters. In the case of triplet emission, also known as phosphorescence, high internal quantum yields of up to 100% can be achieved if the singlet state, which is also excited and is energetically above the triplet state, is able to relax completely into the triplet state and radiation-free competing processes remain unimportant. However, many triplet emitters which are basically suitable for opto-electronic applications have the disadvantage of a long emission lifetime, which can result in a drop in efficiency, for example in OLED devices provided with emitters of this type.

Yersin et al. in WO 2010/006681 A1 have proposed organotransition-metal compounds which have a very small energetic separation $\Delta E$ between the lowest triplet state and the higher singlet state and in which efficient re-occupation from the efficiently occupied $T_1$ state into the $S_1$ state can therefore already occur at room temperature. This re-occupation opens a fast emission channel from the short-lived $S_1$ state, which enables the total emission lifetime to be significantly reduced. Complexes containing metal centres having a $d^8$-electron configuration, i.e., in particular, based on the very expensive metals rhodium, iridium, palladium, platinum and gold, have been described as particularly suitable for this purpose.

The present invention was based on the object of providing organotransition-metal complex compounds based on readily available and very inexpensive transition metals which are ideally at least equal to the organotransition-metal complex compounds known from WO 2010/006681 in their physical properties, such as colour purity, emission decay time and quantum efficiency.

The present invention relates to the electronic device comprising a metal complex compound having at least one bidentate ligand containing an N donor and a P donor having the formula I

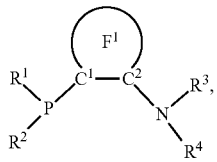

formula I in which
the carbons $C^1$ and $C^2$ are part of an aromatic or non-aromatic ring system $F^1$,
P and N are phosphorus and nitrogen,
$R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and
$R^1$ and $R^2$ are, independently of one another, an atom or radical from the group comprising hydrogen, halogen, R—, RO—, RS—, RCO—, RCOO—, RNH—, $R_2N$—, RCONR— and —$Si(R)_x(OR)_{3-X}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

The present invention likewise relates to a process for the production of the electronic device according to invention which comprises printing a metal complex compound having the at least one ligand of the formula I onto a substrate. The present invention relates to a process for the generation of light of a certain wavelength, comprising the step of providing a metal complex compound having a ligand of the formula I

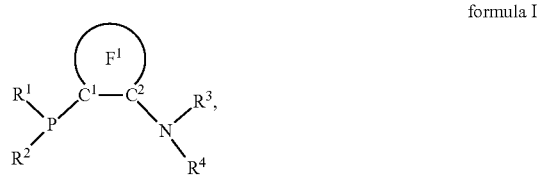

formula I in which
the carbons $C^1$ and $C^2$ are part of an aromatic or non-aromatic ring system $F^1$,
P and N are phosphorus and nitrogen,
$R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and
$R^1$ and $R^2$ are, independently of one another, an atom or radical from the group comprising hydrogen, halogen, R—, RO—, RS—, RCO—, RCOO—, RNH—, $R_2N$—, RCONR— and —$Si(R)_x(OR)_{3-X}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

The present invention also relates to a process for the generation of blue emission which comprises utilizing the metal complex compound having a ligand of the formula I

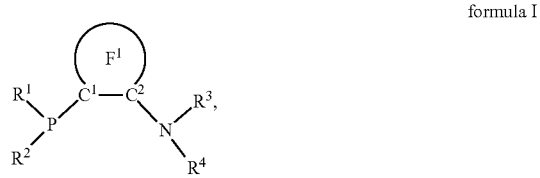

formula I in which
the carbons $C^1$ and $C^2$ are part of an aromatic or non-aromatic ring system $F^1$, P and N are phosphorus and nitrogen, where the nitrogen is in $sp^2$-hybridized form, $R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and $R^1$ and $R^2$ are, independently of one another, an atom or radical from the group comprising hydrogen, halogen, R—, RO—, RS—, RCO—, RCOO—, RNH—, $R_2N$—, RCONR— and —$Si(R)_x(OR)_{3-X}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

Preferred embodiments of the device according to the invention are (1) wherein the metal complex compound is mononuclear or polynuclear;

(2) wherein the metal complex compound is mononuclear or polynuclear, which has one to six metal centres;

(3) wherein the metal complex compound is mononuclear or polynuclear, which has one or two, metal centres;

(4) wherein the metal complex compound contains at least one of the metals Cu or Ag;

(5) wherein the metal complex compound is in the ionic form and contains, besides a Cu or Ag ion, at least one further metal from the group with Cu, Ag, Au, Pd, Pt, Rh, Ir, Re, Os, Mo, W or Zn;

(6) wherein the metal complex compound has the formula II or the formula III

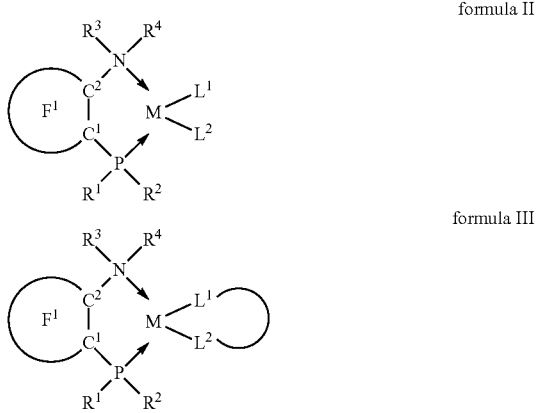

formula II formula III in which
$N, P, C^1, C^2, R^1$ to $R^4$ and $F^1$ are defined as in formula I, M is a metal from the group with Cu, Ag, Au, Pd, Pt, Rh, Ir, Re, Os, Mo, W and Zn and $L^1$ and $L^2$ are, independently of one another, a bridging and/or non-bridging ligand;

(7) wherein the metal complex compound has the formula IV

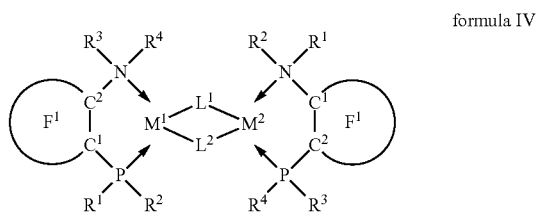

formula IV in which
$N, P, C^1, C^2, R^1$ to $R^4$ and $F^1$ are defined as in formula I,
$M^1$ and $M^2$=a metal from the group with Cu, Ag, Au, Pd, Pt, Rh, Ir, Re, Os, Mo, W and Zn (independently of one another) and
$L^1$ and $L^2$ are, independently of one another, bridging ligands;

(8) wherein the metal complex compound has a ΔE separation between the lowest triplet state and the higher singlet state of between 50 $cm^{-1}$ and 3000 $cm^{-1}$;

(9) wherein the device is selected from the group consisting of an organic electroluminescent device, a light-emitting electrochemical cell, an organic solar cell, an organic field-effect transistor and an organic laser;

(10) wherein the device comprises the metal complex compound as constituent of an emitter layer, where the proportion of the metal complex in the emitter layer is between 0.1 and 50% by weight; and

(11) wherein the device comprises the metal complex compound as constituent of an absorber layer, where the proportion of the metal complex in the absorber layer is between 30 and 100% by weight.

The wording of all claims is hereby incorporated into this description by way of reference.

A BRIEF DESCRIPTION OF THE FIGURES

Figure 1:
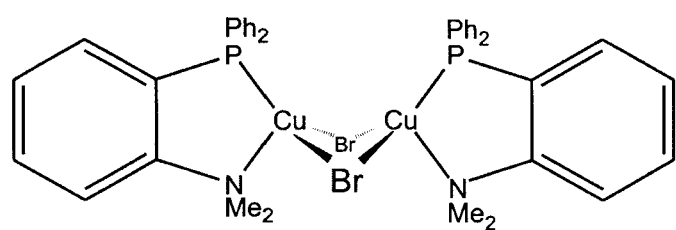
FIG. 1 illustrates the structure of the dinuclear bromine-bridged copper complex (1) and the emission spectrum of this complex.
Figure 1:
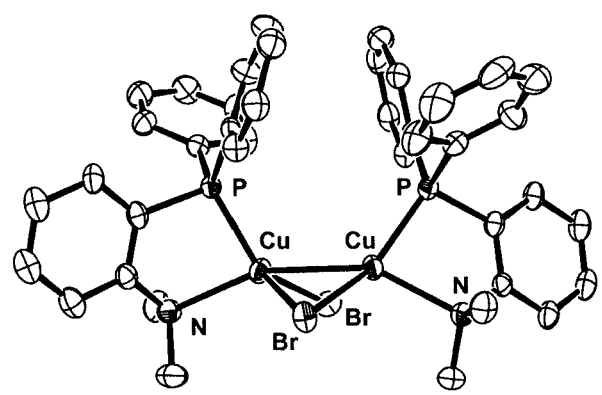
Figure 1:
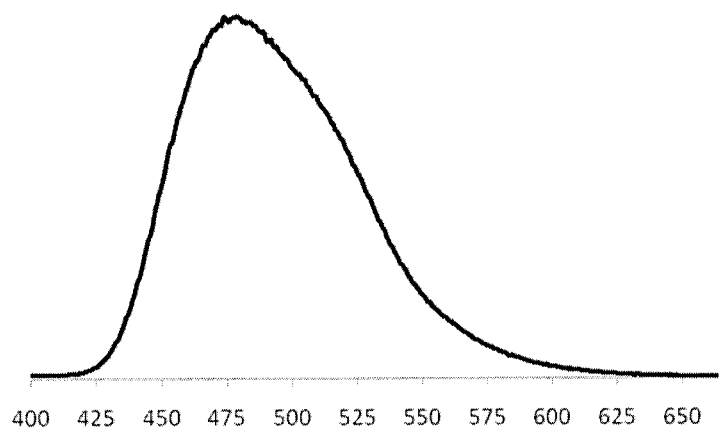

An electronic device according to the invention is distinguished by the fact that it comprises a metal complex compound having at least one bidentate ligand containing an N donor and a P donor having the formula I

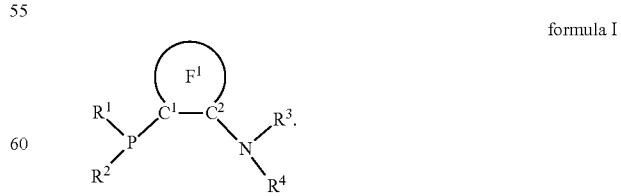

formula I

In this formula, the variables are preferably defined as follows:
the carbons $C^1$ and $C^2$ are part of an aromatic or non-aromatic ring system $F^1$, P and N are phosphorus and nitrogen, where the nitrogen is in sp$^2$-hybridised form, the radicals R$^3$ and R$^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and R$^1$ and R$^2$ are, independently of one another, an atom or radical from the group comprising hydrogen, halogen, R—, RO—, RS—, RCO—, RCOO—, RNH—, R$_2$N—, RCONR— and —Si(R)$_X$(OR)$_{3-X}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

In particularly preferred embodiments, one of the radicals R$^3$ or R$^4$ is an alkyl, cycloalkyl, alkylcycloalkyl, heteroalkyl, heterocycloalkyl or heteroalkylcycloalkyl radical having up to 40 C atoms while the other is a hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms.

Each of the alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radicals may, in preferred embodiments, have one or more halogen, hydroxyl, thiol, carbonyl, keto, carboxyl, cyano, sulfone, nitro, amino and/or imino functions.

The expression alkyl radical having up to 40 C atoms relates, in particular, to a saturated, straight-chain or branched hydrocarbon group which has 1 to 20 carbon atoms, preferably 1 to 12 carbon atoms, particularly preferably 1 to 6 carbon atoms. Examples thereof are the methyl, ethyl, propyl, isopropyl, isobutyl, t-butyl, n-hexyl, 2,2-dimethylbutyl or n-octyl group.

The expressions alkenyl and alkynyl radical having up to 40 C atoms relate, in particular, to at least partially unsaturated, straight-chain or branched hydrocarbon groups which have 2 to 20 carbon atoms, preferably 2 to 12 carbon atoms, particularly preferably 2 to 6 carbon atoms. Examples thereof are the ethenyl, allyl, acetylenyl, propargyl, isoprenyl or hex-2-enyl group.

The expressions cycloalkyl, cycloalkenyl and cycloalkynyl radical having up to 40 C atoms relate, in particular, to saturated or partially unsaturated cyclic groups which have one or more rings which have, in particular, 3 to 14 ring carbon atoms, particularly preferably 3 to 10 ring carbon atoms. Examples thereof are the cyclopropyl, cyclohexyl, tetralin or cyclohex-2-enyl group.

The expression heteroalkyl radical having up to 40 C atoms relates, in particular, to an alkyl, an alkenyl or an alkynyl group in which one or more (preferably 1, 2 or 3) carbon atoms or CH or CH$_2$ groups have been replaced by an oxygen, nitrogen, phosphorus and/or sulfur atom. Examples thereof are alkyloxy groups, such as methoxy or ethoxy, or tertiary amine structures.

The expression heterocycloalkyl radical having up to 40 C atoms relates, in particular, to a cycloalkyl, cycloalkenyl or cycloalkynyl group in which one or more (preferably 1, 2 or 3) ring carbon atoms or ring CH or CH$_2$ groups have been replaced by an oxygen, nitrogen, phosphorus and/or sulfur atom, and can stand, for example, for the piperidine or N-phenylpiperazine group.

The expression aryl radical having up to 40 C atoms relates, in particular, to an aromatic group which has one or more rings which contain, in particular, 5 or 6 to 14 ring carbon atoms, particularly preferably 5 or 6 to 10 ring carbon atoms. Examples thereof are a phenyl, naphthyl or 4-hydroxyphenyl group.

The expression heteroaryl radical having up to 40 C atoms relates, in particular, to an aryl group in which one or more (preferably 1, 2 or 3) ring carbon atoms or ring CH or CH$_2$ groups have been replaced by an oxygen, nitrogen, phosphorus and/or sulfur atom. Examples thereof are the 4-pyridyl, 2-imidazolyl or the 3-pyrazolyl group.

The expressions aralkyl or heteroaralkyl radical having up to 40 C atoms relate, in particular, to groups which, in accordance with the above definitions, contain both aryl and/or heteroaryl groups and also alkyl, alkenyl, alkynyl or heteroalkyl groups. Examples thereof are arylalkyl, arylalkenyl, arylalkynyl, arylheteroalkyl, arylheteroalkenyl, arylheteroalkynyl, heteroarylheteroalkyl, heteroarylheteroalkenyl, heteroarylheteroalkynyl, arylcycloalkyl, heteroarylcycloalkyl, arylheterocycloalkyl, heteroarylheterocycloalkyl, heteroarylcycloalkenyl, arylcycloalkenyl, arylcycloalkynyl, heteroarylcycloalkynyl, arylheteroalkenyl, heteroarylheteroalkenyl, arylheteroalkynyl, heteroarylheteroalkynyl, heteroarylalkyl, heteroarylalkenyl and heteroarylalkynyl groups.

The expressions alkylcycloalkyl or heteroalkylcycloalkyl radical having up to 40 C atoms relate to groups which, in accordance with the above definitions, contain both cycloalkyl or heterocycloalkyl and also alkyl, alkenyl, alkynyl and/or heteroalkyl groups. Examples of such groups are alkylcycloalkyl, alkenylcycloalkyl, alkynylcycloalkyl, alkylheterocycloalkyl, alkenylheterocycloalkyl, alkynylheterocycloalkyl, heteroalkylcycloalkyl, heteroalkenylcycloalkyl, heteroalkylheterocycloalkyl, heteroalkenylheterocycloalkyl, heteroalkynylcycloalkyl, and heteroalkynylheterocycloalkyl groups.

Examples which may be mentioned here of a group of the general formula Si(R)$_X$(OR)$_{3-X}$ described above, where X=1, 2 or 3, are organo-silicon radicals, such as —Si(OMe)$_3$, —SiMe(OMe)$_2$, —SiMe$_2$(OMe), —Si(OPh)$_3$, —SiMe(OPh)$_2$, —SiMe$_2$(OPh), —Si(OEt)$_3$, —SiMe(OEt)$_2$, —SiMe$_2$(OEt), —Si(OPr)$_3$, —SiMe(OPr)$_2$, —SiMe$_2$(OPr), —SiEt(OMe)$_2$, —SiEtMe(OMe), —SiEt$_2$(OMe), —SiPh(OMe)$_2$, —SiPhMe(OMe), —SiPh$_2$(OMe), —SiMe(OC(O)Me)$_2$, —SiMe$_2$(OC(O)Me), —SiMe(O—N=CMe$_2$)$_2$ or —SiMe$_2$-(O—N=CMe$_2$), where the abbreviations Me stand for methyl, Ph for phenyl, Et for ethyl and Pr for iso- or n-propyl.

F$^1$ is preferably a cycloalkyl group, cycloalkenyl group, cycloalkynyl group, aryl group, heteroaryl group, aralkyl group and/or a heteroaralkyl group in accordance with the above definition. F1 is particularly preferably an aromatic ring system, in particular a substituted or unsubstituted benzene ring or einen a substituted or unsubstituted naphtyl radical.

In particularly preferred embodiments, P can be a ring atom of a ring system of an aromatic or non-aromatic nature. In this case, R$^1$ and R$^2$ in formula I are fragments of the corresponding ring system. R$^1$, R$^2$ and P then preferably form a heterocycloalkyl, heteroaryl, heteroaralkyl or heteroalkylcycloalkyl radical or at least part of one such, as is described above.

By contrast, the nitrogen N in formula I, as mentioned above, is always sp$^3$-hybridised and is thus also not part of an aromatic system. However, it is entirely possible for N to be a ring atom of a ring system of a non-aromatic nature. In this case, R$^3$ and R$^4$ in formula I are fragments of the corresponding ring system. $R^3$, $R^4$ and N then preferably form a heterocycloalkyl or heteroalkylcycloalkyl radical or at least a part of such a radical, as is described above.

$R^3$ and $R^4$ are particularly preferably both alkyl or heteroalkyl radicals or part of one of the ring systems of a non-aromatic nature mentioned or one of the two is an alkyl or heteroalkyl radical and the other is an aryl, heteroaryl, aralkyl or heteroaralkyl radical.

The metal complex compound can in principle be a mononuclear or polynuclear metal complex compound. The metal complex compound preferably has between 1 and 6, in particular between 1 and 2, metal centres.

In principle, the metal complex compound can be a copper, silver, gold, palladium, platinum, rhodium, iridium, rhenium, osmium, molybdenum, tungsten or zinc complex. The metals are preferably in the form of cations, in particular they are singly to sextuply positively charged.

The metal complex compound particularly preferably contains at least one of the metals Cu or Ag, in particular in ionic form, as metallic centre.

The electronic device according to the invention particularly preferably comprises metal complexes of the formulae II and/or III:

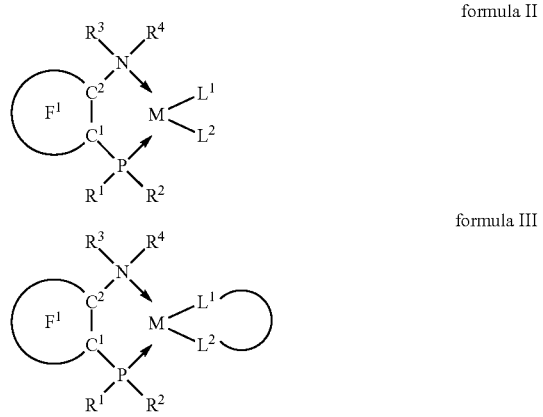

formula II formula III

In this formula,
N, P, $C^1$, $C^2$, $R^1$ to $R^4$ and $F^1$ are defined as in formula I,
M=a metal from the group with Cu, Ag, Au, Pd, Pt, Rh, Ir, Re, Os, Mo, W and Zn and
$L^1$ and $L^2$ are, independently of one another, a bridging and/or non-bridging ligand.

Non-bridging ligands $L^1$ and $L^2$ in the present case are intended to be taken to mean ligands which do not bond simultaneously to two or more metal centres. Even though such ligands are not structure-forming, they may have a great influence on the separations between the metal centres of a polynuclear complex in that they increase or reduce the electron densities at the metal centres. The ligands are important for the saturation of the coordination sphere of the metal or for charge equalisation or for both. These ligands $L^1$ and $L^2$ can therefore be neutral or anionic. Furthermore, the ligands $L^1$ and $L^2$ can be monodentate or constituents of a bidentate ligand.

Suitable neutral, monodentate ligands $L^1$ and $L^2$ are preferably selected from the group with carbon monoxide, nitrogen monoxide, nitriles (RCN), isonitriles (RNC), such as, for example, t-butyl isonitrile, cyclohexyl isonitrile, adamantyl isonitrile, phenyl isonitrile, mesityl isonitrile and 2,6-dimethylphenyl isonitrile, ethers, such as, for example, dimethyl ether and diethyl ether, selenides, amines, such as, for example, trimethylamine, triethylamine and morpholine, imines (RN=CR'), phosphines, such as, for example, triphenylphosphine, phosphites, such as, for example, trimethyl phosphite, arsines, such as, for example, trifluoro-arsine, trimethylarsine and triphenylarsine, stibines, such as, for example, trifluorostibine or triphenylstibine, and nitrogen-containing heterocycles, such as, for example, pyridine, pyridazine, pyrazine, pyrimidine and triazine.

Suitable anionic, monodentate ligands $L^1$ and $L^2$ are preferably selected from the group with hydride, deuteride, the halides F, Cl, Br and I, azide, alkylacetylides, aryl- or heteroarylacetylides, alkyl, aryl and heteroaryl, as have been defined above, hydroxide, cyanide, cyanate, isocyanate, thiocyanate, isothiocyanate, aliphatic or aromatic alcoholates, such as, for example, methanolate, ethanolate, propanolate and phenolate, aliphatic or aromatic thioalcoholates, such as, for example, methanethiolate, ethanethiolate, propanethiolate and thiophenolate, amides, such as, for example, dimethylamide, diethylamide and morpholide, carboxylates, such as, for example, acetate, trifluoroacetate, propionate and benzoate, anionic, nitrogen-containing heterocycles, such as, for example, pyrrolide, imidazolide, pyrazolide, aliphatic and aromatic phosphides or aliphatic or aromatic selenides.

Suitable di- or trianionic ligands $L^1$ and $L^2$ are, for example, $O^{2-}$, $S^{2-}$ or $N^{3-}$.

Suitable neutral or mono- or dianionic bidentate ligands are preferably selected from the group with diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine or 2-[1-(ethylimino)ethyl]pyridine, diimines, such as, for example, 1,2-bis(methylimino)ethane, 1,2-bis(ethylimino)ethane, 1,2-bis(isopropylimino)ethane, 2,3-bis(methyl-imino)butane, 2,3-bis(isopropylimino)butane or 1,2-bis(2-methylphenylimino)ethane, heterocycles containing two nitrogen atoms, such as, for example, 2,2'-bipyridine or o-phenanthroline, diphosphines, such as, for example, bis(diphenylphosphino)methane, bis(diphenylphosphino)ethane, bis(dimethylphosphino)methane, bis(dimethylphosphino)ethane, bis(diethylphosphino)methane or bis(diethylphosphino)ethane, 1,3-diketonates derived from 1,3-diketones, such as, for example, acetylacetone, benzoylacetone, 1,5-diphenylacetylacetone, dibenzoylmethane and bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol and dithiolates derived from dithiols, such as, for example, 1,2-ethylenedithiol and 1,3-propylenedithiol.

It is furthermore also possible to employ bidentate monoanionic ligands which, with the metal, have a cyclometallated five-membered ring or six-membered ring having at least one metal-carbon bond, in particular a cyclometallated five-membered ring. These are, in particular, ligands as are generally used in the area of phosphorescent metal complexes for organic electroluminescent devices, i.e. ligands of the phenylpyridine, naphthylpyridine, phenylquinoline, phenylisoquinoline, etc., type, each of which may be substituted or unsubstituted. A multiplicity of such ligands are known to the person skilled in the art in the area of phosphorescent electroluminescent devices, and he will be able to select further ligands of this type without inventive step.

If the ligands L¹ and L² are non-bridging ligands, the metal complex compounds depicted in the formulae II and III are then preferably metal complex compounds having a metallic centre. If the ligands L¹ and L² are, by contrast, bridging ligands, the structure depicted in formula II can then also be the fragment of a polynuclear complex compound, for example a dinuclear complex, as depicted in formula IV:

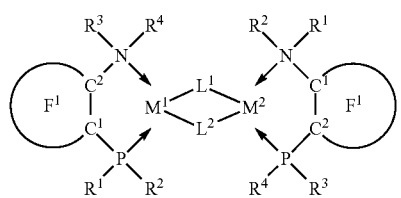

formula IV

In this formula,

N, P, C¹, C², R¹ to R⁴ and F¹ are defined as in formula I,
M¹ and M² are each a metal from the group with Cu, Ag, Au, Pd, Pt, Rh, Ir, Re, Os, Mo, W and Zn (independently of one another) and
L¹ and L² are, independently of one another, bridging ligands.

Depending on the nature of L¹ and L², more than dinuclear complex compounds can also readily be achieved.

Bridging ligands L¹ and L² in the present case are intended to be taken to mean ligands which bond simultaneously to two or more metal centres and are thus structure-forming. These are thus used, in particular, if the complex used in accordance with the invention is a polynuclear complex. Suitable bridging ligands generally contain at least two donor groups and one bridge fragment connecting the donor groups. The donor group is an atom or an atom group which bonds to the metal atom. The two donor groups may be identical or different, i.e. asymmetrical ligands may also be used Bridging ligands L¹ and L² may also be either neutral or anionic. In the latter case, either the donor groups or the bridge fragment carry a negative charge.

Neutral, bridging ligands L¹ and L² contain as donor groups, in particular, groups from the series with R₂N—, R₂P—, R₂As—, R₂N—, CN—, NC—, RO—, RS—, RSe— and RN=. ("—" or "=" denotes the bonding mode by means of which the donor group is bonded to the bridge, R preferably a $C_1$- to $C_{40}$-hydrocarbon, as has been defined above). Suitable as bridge fragment is likewise a hydrocarbon as has already been described, preferably having a maximum of 6 C atoms.

In the case of anionic, bridging ligands L¹ and L², one or both donor groups are negatively charged, or the bridge fragment carries the charge. Frequently used anionic donor groups are: O—, NR— or C≡C—. Examples of anionic, bridging ligands L¹ and L² are, for example,

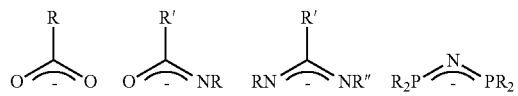

In these formulae, R and R' stand, in particular, for an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, as has already been defined above.

For the purposes of the present invention, the bridging and/or non-bridging ligands L¹ and L² used are particularly preferably halide, pseudohalide, alkoxide, alkyl, silyl, phosphide, amide, amine or phosphine, acetylacetonate or pyrazolato ligands.

Mononuclear metal complex compounds according to the invention can contain up to three ligands of the formula I, polynuclear metal complex compounds according to the invention may optionally also contain more. If desired, metal complex compounds according to the invention may also contain bridging and/or non-bridging ligands L³ and/or L⁴ and optionally also further ligands, if the ligand(s) of the formula I and, if used, the ligands L¹ and L² have not yet saturated all free valences of the metal centre(s). The ligands L³ and/or L⁴ are optionally selected independently of one another and of L¹ and L², but are preferably defined chemically the same as L¹ and L².

The metal complex compounds selected are particularly preferably organic transition-metal compounds which have a ΔE separation between the lowest triplet state and the higher singlet state of between 50 $cm^{-1}$ and 3000 $cm^{-1}$, i.e. have the same properties in this respect as the complexes described in WO 2010/006681. Regarding the calculation or measurement of the energy separation ΔE, reference is made to the statements in this respect in WO 2010/006681.

The device according to the invention is, in particular, a device from the group consisting of organic electroluminescent devices (OLEDs), light-emitting electrochemical cells (LEECs), organic solar cells (OSCs), organic field-effect transistors and organic lasers. Further fields of application which come into question are OLED sensors, in particular gas and vapour sensors which are not hermetically shielded from the outside.

In particular if the electronic device according to the invention is an organic electroluminescent device, it is preferred for the device to comprise the metal complex compound as constituent of an emitter layer. The proportion of the metal complex compound in the emitter layer is in this case preferably between 0.1 and 50% by weight.

As is known, OLEDs are built up from a plurality of layers. A layer-like anode, for example consisting of indium tin oxide (ITO), is usually located on a substrate, such as a glass sheet. A hole-transport layer (HTL) is arranged on this anode. A layer of PEDOT/PSS (poly(3,4-ethylenedioxy-thiophene) polystyrene sulfonate), which serves to lower the injection barrier for holes and prevents indium from diffusing into the junction, may optionally also be located between the anode and the hole-transport layer. The emitter layer, which in the present case comprises the metal complex described above having the at least one bidentate ligand, is very generally applied to the hole-transport layer. Under certain circumstances, the emitter layer may also consist of this complex. Finally, an electron-transport layer (ETL) is applied to the emitter layer. A cathode layer, for example consisting of a metal or metal alloy, is in turn applied thereto by vapour deposition in a high vacuum. As protective layer and in order to reduce the injection barrier for electrons, a thin layer of lithium fluoride, caesium fluoride or silver may optionally also be applied between cathode and the ETL by vapour deposition.

In operation, the electrons (=negative charge) migrate from the cathode in the direction of the anode, which provides the holes (=positive charge). In the ideal case, holes and electrons meet in the emitter layer, which is why this is also called the recombination layer. Electrons and holes form a bonded state, which is called exciton. A metal complex compound, such as that described in the present case, can be excited by an exciton by energy transfer. This can be converted into the ground state and can emit a photon in the process. The colour of the emitted light depends on the energy separation between excited state and ground state and can be varied in a targeted manner by variation of the complex or complex ligands.

In particular if the device according to the invention is an organic solar cell, it is preferred for the device to comprise the metal complex compound as constituent of an absorber layer, where the proportion of the metal complex compound in the absorber layer is preferably between 30 and 100% by weight. An organic solar cell is a solar cell which consists at least predominantly of organic materials, i.e. of hydrocarbon compounds.

As in the case of OLEDs, two electrodes are also provided in organic solar cells. The absorber layer in which the metal complex compound described in the present application is used is arranged between these.

As already mentioned, the metal complex compound described in the present case can emit light. By variation of the ligands and/or of the metal nucleus or nuclei, the ΔE separation between the lowest triplet state the higher singlet state can be varied, so that it is in principle possible to set the wavelength of the emitted light to defined values, in particular also to very short-wave values, so that blue light is emitted. In particular with copper complexes which have the bidentate complex ligand described, excellent results have been achieved in this respect. Correspondingly, the present invention also encompasses a process for the generation of light of a certain wavelength or for the generation of blue emission, where in both cases the metal complex described having the bidentate ligand described having an N donor and a P donor is provided and used.

The complex compounds described are generally very readily soluble in organic solvents, such as benzene or toluene. This opens up the possibility of printing basically any desired substrate with the complex compounds. Correspondingly, the present invention also relates to a process for the production of an electronic device as described above, in which the metal complex compound described having at least one ligand of the formula I is printed onto a substrate.

Further features of the invention arise from the following description of preferred embodiments. It should be explicitly emphasised at this point that all optional aspects of the devices according to the invention or the processes according to the invention described in the present application can, in an embodiment of the invention, each be achieved individually or in combination with one or more of the further optional aspects described. The following description of preferred embodiments serves merely for explanation and for better understanding of the invention and should in no way be understood as restrictive.

WORKING EXAMPLE

For the preparation of metal complex compounds having at least one bidentate ligand containing an N donor and a P donor having the formula I, the ligand was stirred for several hours with an excess of a corresponding metal halide compound in toluene. The metal complex compounds were subsequently filtered and isolated by cold crystallisation.

For example, dinuclear complex compounds having the following formula were synthesised by this procedure:

$[(Me_2N\text{-}o\text{-}C_6H_4\text{—}PPh_2)CuBr]_2$     (1)

$[(Me_2N\text{-}o\text{-}C_6H_4\text{—}PPh_2)CuCl]_2$     (2)

$[(Me_2N\text{-}o\text{-}C_6H_4\text{—}PPh_2)CuI]_2$     (3)

The structure of the dinuclear bromine-bridged copper complex (1) and the emission spectrum of this complex are shown in FIG. 1. The complex exhibited green to blue (511 to 467 nm) luminescence, exhibited an excellent decay behaviour and was easy to prepare.

Figure 2:
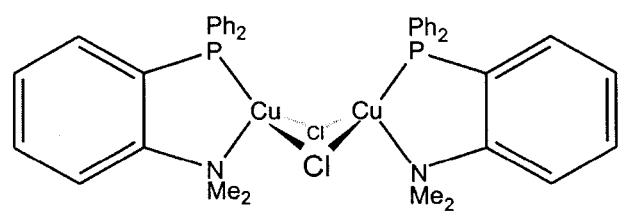
FIG. 2 illustrates the structure of the dinuclear chlorine-bridged copper complex (2) and the emission spectrum of this complex.
Figure 2:
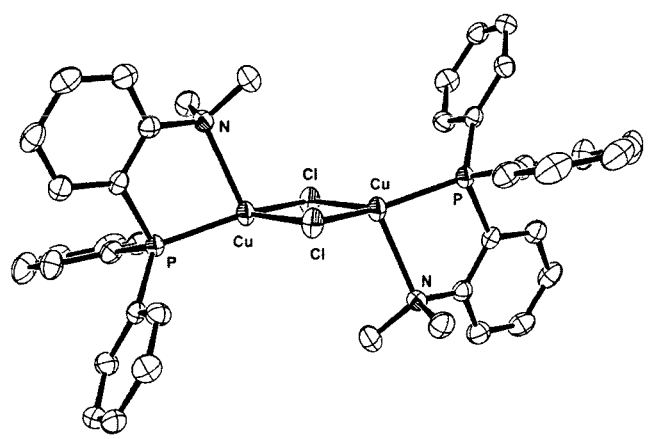
Figure 2:
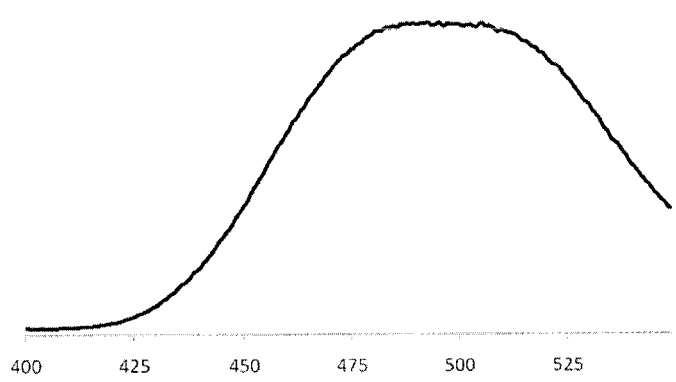

The structure of the dinuclear chlorine-bridged copper complex (2) and the emission spectrum of this complex are shown in FIG. 2.

Figure 3:
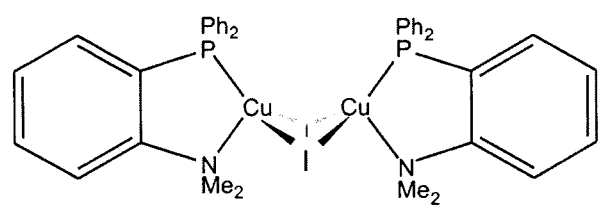
FIG. 3 illustrates the structure of the dinuclear iodine-bridged copper complex (3) and the emission spectrum of this complex.
Figure 3:
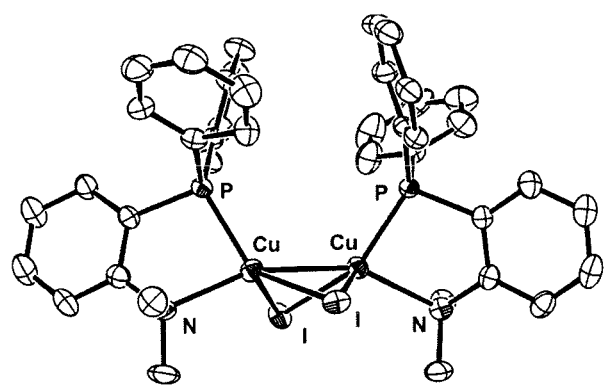
Figure 3:
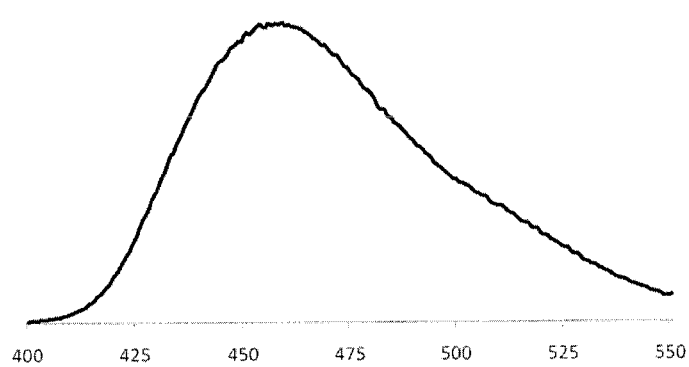

The structure of the dinuclear iodine-bridged copper complex (3) and the emission spectrum of this complex are shown in FIG. 3.

Depending on the bridge atom (chlorine, bromine and iodine), the quantum yield was between 50% (Cl) and 75% (I) with an emission decay duration of 7, 3 and 5 μs.

The invention claimed is:

1. An electronic device comprising a polynuclear metal complex compound having at least one bidentate ligand containing an N donor and a P donor having the formula I

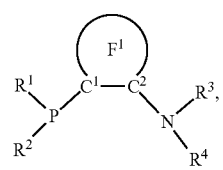

formula I in which
   the carbons $C^1$ and $C^2$ are part of an aromatic or non-aromatic ring system $F^1$,
   P and N are phosphorus and nitrogen,
   $R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and $R^1$ and $R^2$ are, independently of one another, an atom or radical from the group comprising hydrogen, halogen, R—, RO—, RS—, RCO—, RCOO—, RNH—, $R_2N$—, RCONR— and —$Si(R)_x(OR)_{3-X}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

2. The device according to claim 1, wherein the metal complex compound has up to six metal centres.

3. The device according to claim 1, wherein the metal complex compound has two metal centres.

4. The device according to claim 1, wherein the metal complex compound contains at least one of the metals Cu or Ag.

5. The device according to claim 4, wherein the metal complex compound is in the ionic form and contains, besides a Cu or Ag ion, at least one further metal from the group with Cu, Ag, Au, Pd, Pt, Rh, Ir, Re, Os, Mo, W or Zn.

6. An electronic device comprising a metal complex compound which has the formula II or the formula III formula II formula III in which
the carbons $C^1$ and $C^2$ are part of an aromatic or non-aromatic ring system $F^1$, P and N are phosphorus and nitrogen, $R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and $R^1$ and $R^2$ are, independently of one another, an atom or radical from the group comprising hydrogen, halogen, R—, RO—, RS—, RCO—, RCOO—, RNH—, R2N—, RCONR— and —Si(R)X(OR)3-X, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3, M is a metal from the group with Cu, Ag, Au, Pd, Pt, Rh, Ir, Re, Os, Mo, W and Zn and $L^1$ and $L^2$ are, independently of one another, a bridging and/or non-bridging ligand.

7. The device according to claim 1, wherein the metal complex compound has the formula IV formula IV in which
N, P, $C^1$, $C^2$, $R^1$ to $R^4$ and $F^1$ are defined as in formula I,
$M^1$ and $M^2$=a metal from the group with Cu, Ag, Au, Pd, Pt, Rh, Ir, Re, Os, Mo, W and Zn (independently of one another) and $L^1$ and $L^2$ are, independently of one another, bridging ligands.

8. The device according to claim 1, wherein the metal complex compound has a energetic separation (ΔE separation) between the lowest triplet state and the higher singlet state of between 50 $cm^{-1}$ and 3000 $cm^{-1}$.

9. The device according to claim 1, wherein the device is selected from the group consisting of an organic electroluminescent device, a light-emitting electrochemical cell, an organic solar cell, an organic field-effect transistor and an organic laser.

10. The device according to claim 1, wherein the device comprises the metal complex compound as constituent of an emitter layer, where the proportion of the metal complex in the emitter layer is between 0.1 and 50% by weight.

11. The device according to claim 1, wherein the device comprises the metal complex compound as constituent of an absorber layer, where the proportion of the metal complex in the absorber layer is between 30 and 100% by weight.

12. A process for the production of the electronic device according to claim 1, which comprises printing a metal complex compound having the at least one ligand of the formula I onto a substrate.

13. A process for the generation of light of a certain wavelength, comprising the step of providing a polynuclear metal complex compound having a ligand of the formula I formula I in which
the carbons $C^1$ and $C^2$ are part of an aromatic or non-aromatic ring system $F^1$,
P and N are phosphorus and nitrogen,
$R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and $R^1$ and $R^2$ are, independently of one another, an atom or radical from the group comprising hydrogen, halogen, R—, RO—, RS—, RCO—, RCOO—, RNH—, R$_2$N—, RCONR— and —Si(R)$_x$(OR)$_{3-x}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

14. A process for the generation of blue emission which comprises utilizing a polynuclear metal complex compound having a ligand of the formula I

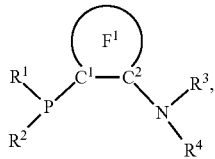

formula I in which
the carbons $C^1$ and $C^2$ are part of an aromatic or non-aromatic ring system $F^1$, P and N are phosphorus and nitrogen, $R^3$ and $R^4$ are, independently of one another, hydrogen or an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms, and $R^1$ and $R^2$ are, independently of one another, an atom or radical from the group comprising hydrogen, halogen, R—, RO—, RS—, RCO—, RCOO—, RNH—, R$_2$N—, RCONR— and —Si(R)$_x$(OR)$_{3-x}$, where R=an alkyl, cycloalkyl, alkenyl, cycloalkenyl, alkynyl, cycloalkynyl, alkylcycloalkyl, heteroalkyl, heterocycloalkyl, heteroalkylcycloalkyl, aryl, heteroaryl, aralkyl or heteroaralkyl radical having up to 40 C atoms and X=1, 2 or 3.

* * * * *